(12) United States Patent
Matsuno et al.

(10) Patent No.: US 8,998,825 B2
(45) Date of Patent: Apr. 7, 2015

(54) ENDOSCOPE TREATMENT SYSTEM

(71) Applicant: Olympus Medical Systems Corp., Tokyo (JP)

(72) Inventors: Kiyotaka Matsuno, Sagamihara (JP); Junichi Muramatsu, Sagamihara (JP); Hidenori Yoshida, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 14/091,909

(22) Filed: Nov. 27, 2013

(65) Prior Publication Data

US 2014/0171833 A1    Jun. 19, 2014

Related U.S. Application Data

(63) Continuation of application No. PCT/JP2013/065480, filed on Jun. 4, 2013.

(60) Provisional application No. 61/671,247, filed on Jul. 13, 2012.

(51) Int. Cl.
| | |
|---|---|
| *A61B 5/00* | (2006.01) |
| *A61B 1/00* | (2006.01) |
| *A61B 1/018* | (2006.01) |
| *A61B 17/00* | (2006.01) |
| *A61B 18/14* | (2006.01) |

(Continued)

(52) U.S. Cl.
CPC ....... *A61B 17/00234* (2013.01); *A61B 1/00128* (2013.01); *A61B 1/018* (2013.01); *A61B 18/1492* (2013.01); *A61B 19/026* (2013.01); *A61B 2017/00296* (2013.01); *A61B 2017/22038* (2013.01); *A61B 2018/141* (2013.01); *A61B 2018/144* (2013.01); *A61B 2019/0267* (2013.01); *A61B 2019/267* (2013.01); *A61M 25/002* (2013.01); *A61M 25/09* (2013.01)

(58) Field of Classification Search
USPC .......................................................... 600/585
See application file for complete search history.

(56) References Cited

U.S. PATENT DOCUMENTS

| | | | | |
|---|---|---|---|---|
| 5,314,407 | A | * | 5/1994 | Auth et al. ...................... 604/22 |
| 5,507,300 | A | | 4/1996 | Mukai et al. |

(Continued)

FOREIGN PATENT DOCUMENTS

| | | |
|---|---|---|
| JP | A-2002-282275 | 10/2002 |
| JP | A-2004-254879 | 9/2004 |

(Continued)

OTHER PUBLICATIONS

Jul. 30, 2013 International Search Report issued in International Application No. PCT/JP2013/065480.

*Primary Examiner* — Max Hindenburg
(74) *Attorney, Agent, or Firm* — Oliff PLC

(57) ABSTRACT

The endoscope treatment system includes an endoscope treatment tool that has an operating section including a distal end and a proximal end, and a sheath that is connected to the distal end of the operating section and is formed with a lumen into which the guide wire is capable of being inserted; a guide wire holder that has a tube member, in which the guide wire is accommodated, and that is circumferentially wound; and a fixing member that couples the operating section to the guide wire holder so that the distal end and the proximal end of the operating section are located outside the circumference of the guide wire holder.

13 Claims, 10 Drawing Sheets

(51) Int. Cl.
*A61B 19/02* (2006.01)
*A61B 17/22* (2006.01)
*A61B 19/00* (2006.01)
*A61M 25/00* (2006.01)
*A61M 25/09* (2006.01)

(56) References Cited

U.S. PATENT DOCUMENTS

| 5,730,150 | A | * | 3/1998 | Peppel et al. | 600/585 |
| 5,843,002 | A | * | 12/1998 | Pecor et al. | 600/585 |
| 6,606,515 | B1 | * | 8/2003 | Windheuser et al. | 600/434 |
| 7,857,770 | B2 | * | 12/2010 | Raulerson et al. | 600/585 |
| 8,202,254 | B2 | * | 6/2012 | Schweikert et al. | 604/171 |
| 2003/0036712 | A1 | | 2/2003 | Heh et al. | |

FOREIGN PATENT DOCUMENTS

| JP | A-2004-275785 | 10/2004 |
| JP | A-2008-080047 | 4/2008 |
| JP | A-2012-065871 | 4/2012 |
| WO | WO 2005/110187 A1 | 11/2005 |

* cited by examiner

ENDOSCOPE TREATMENT SYSTEM

This application is a continuation claiming priority based on U.S. Pat. Application No. 61/671,247 provisionally filed in the United States on Jul. 13, 2012 and based on PCT/JP2013/065480 filed on Jun. 4, 2013. The contents of both the United States Patent Application and the PCT Application are incorporated herein by reference.

TECHNICAL BACKGROUND

1. Field of the Invention

The present invention relates to an endoscope treatment system.

2. Background Art

In the related art, treatment tools to be used together with endoscopes are known. For example, a high-frequency incision tool used for duodenal papilla sphincter muscle dissection (EST) is disclosed in Japanese Unexamined Patent Application, First Publication No. 2004-275785. Additionally, in EST, it is known that a guide wire is inserted into the bile duct (or pancreatic duct), a high-frequency incision tool is removed after the insertion of the guide wire, and a basket, forceps, or the like is guided to the bile duct (or pancreatic duct) along the guide wire.

As an example of a system of inserting the guide wire, for example, Japanese Unexamined Patent Application, First Publication No. 2008-80047 discloses a system in which a storage portion that stores a guide wire inserted into a treatment target region is attached to a treatment tool.

SUMMARY OF THE INVENTION

According to a first aspect of the present invention, an endoscope treatment system includes an endoscope treatment tool which has an operating section including a distal end and a proximal end, and a sheath that is connected to the distal end of the operating section and is formed with a lumen into which a guide wire is capable of being inserted; a guide wire holder which has a tube member, in which the guide wire is accommodated, and which is wound around a circumference thereof; and a fixing member which couples the operating section to the guide wire holder so that the distal end and the proximal end of the operating section are located outside the circumference of the guide wire holder.

According to a second aspect of the present invention based on the first aspect, the fixing member may detachably couple the operating section to the guide wire holder.

According to a third aspect of the present invention based on the second aspect, the operating section may be provided with a wire insertion port that communicates with the lumen, and the guide wire holder may have a first opening that is formed in the tube member and allows the guide wire to extend therethrough; and a holding fixture that holds the tube member so that the first opening of the tube member faces a second opening that is formed in the wire insertion port and allows the guide wire to be inserted thereinto.

According to a fourth aspect of the present invention based on the third aspect, the operating section may be provided with a wire insertion port that communicates with the lumen, and the fixing member may couple the operating section to the guide wire holder so that the second opening is located inside the circumference of the guide wire holder, in the wire insertion port.

According to a fifth aspect of the present invention based on the fourth aspect, the operating section may have a main body that is formed in a rod shape; and a slider that is attached to the main body and slides along a longitudinal axis of the main body, and the fixing member may couple the operating section and the guide wire holder so that the operating section is adjacent to the guide wire holder in a state where the longitudinal axis is turned to a tangential direction of the circumference.

According to a sixth aspect of the present invention based on the fifth aspect, the holding fixture may be attached to the tube member so as to be capable of switching a state where the first opening of the tube member is located outside the circumference of the guide wire holder and a state where the first opening of the tube member is located inside the circumference of the guide wire holder.

According to a seventh aspect of the present invention based on the sixth aspect, the operating section and the guide wire holder may be detachably coupled by an engagement between a concave portion provided in the fixing member and the tube member.

According to an eighth aspect of the present invention based on the seventh aspect, the endoscope treatment tool and the guide wire holder may be stored in a sterilizing pack in a state where the endoscope treatment tool and the guide wire holder are coupled by the fixing member.

According to a ninth aspect of the present invention based on the third aspect, the operating section may have a main body that is formed in a rod shape; and a slider that is attached to the main body and slides along a longitudinal axis of the main body, and the fixing member may couple the operating section and the guide wire holder so that the operating section is adjacent to the guide wire holder in a state where the longitudinal axis is turned to a tangential direction of the circumference.

PREFERRED EMBODIMENTS

Figure 1:
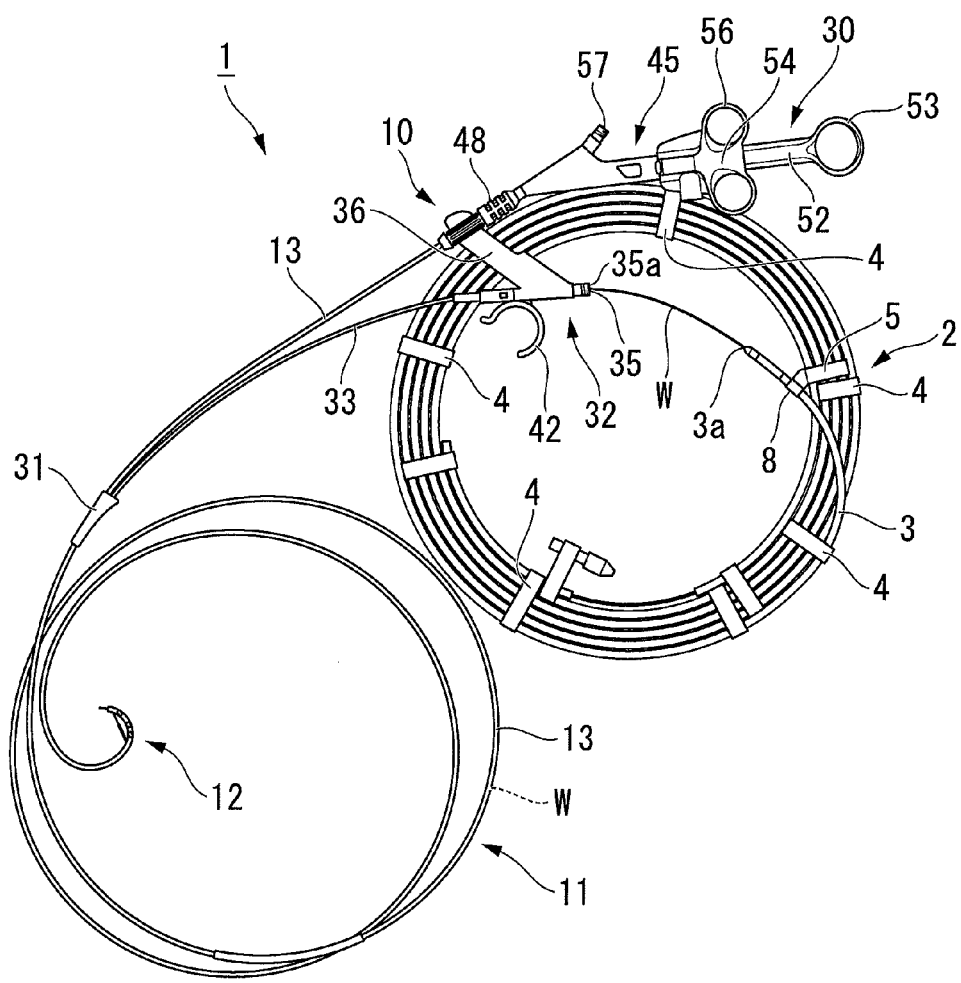
FIG. 1 is an overall view showing an endoscope treatment system of an embodiment of the present invention.

An endoscope treatment system of an embodiment of the present invention will be described. FIG. 1 is an overall view showing the endoscope treatment system of the present embodiment.

As shown in FIG. 1, an endoscope treatment system 1 is a system provided in a state where a guide wire W is attached to a high-frequency incision tool (endoscope treatment tool) 10 in advance. A guide wire W is a wire rod provided in order to guide the high-frequency incision tool 10 to a treatment target region. Additionally, the guide wire W is a wire rod that is flexible and has an excellent torque transmission property. The guide wire W accommodated in a guide wire holder 2 around a flexible tube member 3 is formed so as to be circumferentially wound and is provided in a shape wound along the tube member 3. Also, the guide wire W is delivered from an opening (a first opening) 3a provided at one end of the tube member 3 and is inserted into the inside of the high-frequency incision tool 10 through a wire insertion port 35 (to be described below) that is provided in the high-frequency incision tool 10.

In the present embodiment, the tube member 3 is wound so as to have a spiral shape on the same plane. The spiral shape of the tube member 3 is maintained by a plurality of clips 4. Moreover, the tube member 3 is provided with a holding fixture 5 for defining the position of the opening 3a of the tube member 3 through which the guide wire W is delivered.

Additionally, the holding fixture 5 holds the tube member 3 so that the opening 3a of the tube member 3 faces an opening 35a (a second opening) formed in the wire insertion port 35. The guide wire W is inserted into the opening 35a.

The material of the tube member 3 is not particularly limited. For example, the tube member 3 is formed from a resin, such as polytetrafluoroethylene (PTFE), tetrafluoroethylene hexafluoropropylene resin (FEP), polyethylene, polyolefin, polyamide, vinyl chloride, latex, crude rubber, polysulfone, polyphenylsulfon, polyether imide, POM, PEEK, polycarbonate, and ABS, and synthetic resin materials thereof.

Figure 2:
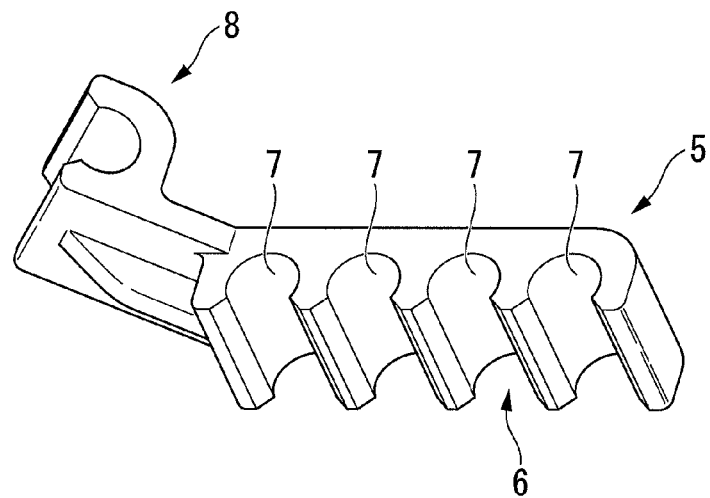
FIG. 2 is a perspective view of a holding fixture attached to a guide wire holder of the endoscope treatment system.
Figure 3:
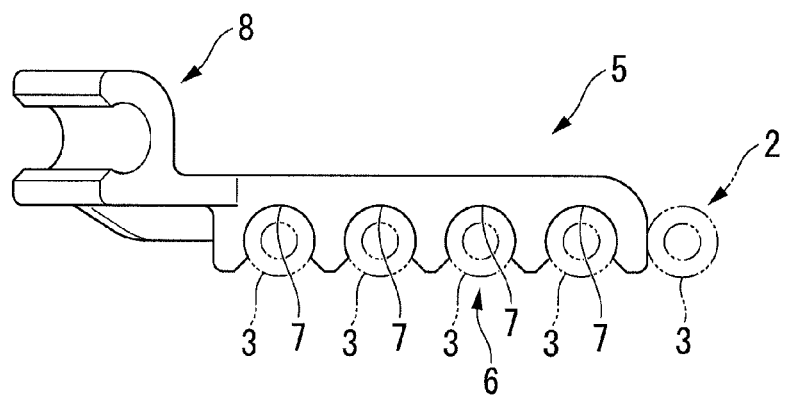
FIG. 3 is a plan view of the holding fixture.
Figure 4:
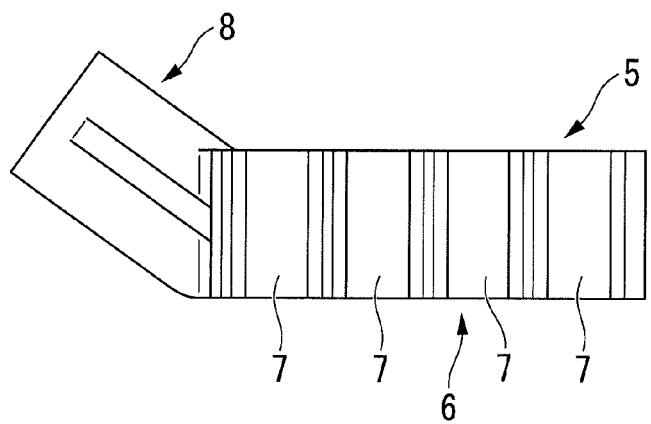
FIG. 4 is a front view of the holding fixture.

FIG. 2 is a perspective view of the holding fixture 5 attached to the guide wire holder 2 of the endoscope treatment system 1. FIG. 3 is a plan view of the holding fixture 5. FIG. 4 is a front view of the holding fixture 5.

As shown in FIGS. 1 to 4, the holding fixture 5 has a first concave portion 6 and a second concave portion 8 that engage an external surface of the tube member 3. The first concave portion 6 engages a portion of an intermediate portion of the tube member 3 that is circumferentially wound. In the present embodiment, the first concave portion 6 has concave portions 7 with the same shape arranged adjacent to each other so as to engage two or more places that are adjacent to each other in the tube member 3, which is circumferentially wound, by friction. Additionally, as shown in FIG. 3, each of the concave portions 7 in the first concave portion 6 has a circular-arc recessed shape that covers more than a semicircle of an external surface of the tube member 3, in a radial cross-section of the tube member 3.

When the tube member 3 is engaged with the first concave portion 6, the tube member 3 is pushed into the first concave portion 6. Accordingly, the tube member 3 is elastically deformed and enters the respective concave portions 7 in the first concave portion 6. Within the first concave portion 6, the tube member 3 is restored to its original shape. For this reason, a space where the guide wire W can enter and leave freely is formed inside the tube member 3 that has entered the first concave portion 6. Additionally, if the tube member 3 is pulled out in the radial direction of the tube member 3 with respect to the first concave portion 6, the tube member 3 can be removed from the first concave portion 6.

In the present embodiment, in the guide wire holder 2 (refer to FIGS. 1 and 3) around which the tube member 3 is wound 5 times, four concave portions 7 are provided adjacent to each other in the holding fixture 5 so as to simultaneously hold four tube members 3 that are adjacent to each other. The number of the concave portions 7 formed in the first concave portion 6 may be smaller than the number of turns of the tube member 3. Accordingly, the first concave portion 6 does not protrude further from an outer periphery of the tube member 3 to the outside, and the guide wire holder 2 becomes compact.

That is, the number of the concave portions 7 formed in the first concave portion 6 may be two or more and smaller than the number of turns of the tube member 3.

As shown in FIGS. 1 to 3, the second concave portion 8 is a concave portion that engages the vicinity of the opening 3a of the tube member 3 from which the guide wire W is delivered. Additionally, the second concave portion 8 has a circular-arc recessed shape that covers more than a semicircle of the external surface of the tube member 3, in the radial cross-section of the tube member 3. Additionally, the second concave portion 8 has a circular-arc recessed shape whose opening is turned to the inside of the circumference formed by the tube member 3, in a state where the first concave portion 6 is attached to the tube member 3. The second concave portion 8 may form a circular arc whose opening is turned in a direction intersecting a plane where the circumference formed by the tube member 3 is present. For example, the second concave portion 8 may form a circular arc whose opening is turned in a direction perpendicular to the plane where the circumference formed by the tube member 3 is present.

The second concave portion 8 causes the opening 3a from which the guide wire W is delivered, further toward the inner side than the tube member 3 located on an innermost peripheral side of the tube members 3 that are circumferentially (spirally in the present embodiment) wound, to locate as a first attachment aspect in the present embodiment (refer to FIG. 1). That is, the tube member 3 is bent at an outermost peripheral portion of the tube member 3 by the holding fixture 5 so as to go from the outer periphery thereof to an inner periphery thereof.

Figure 14:
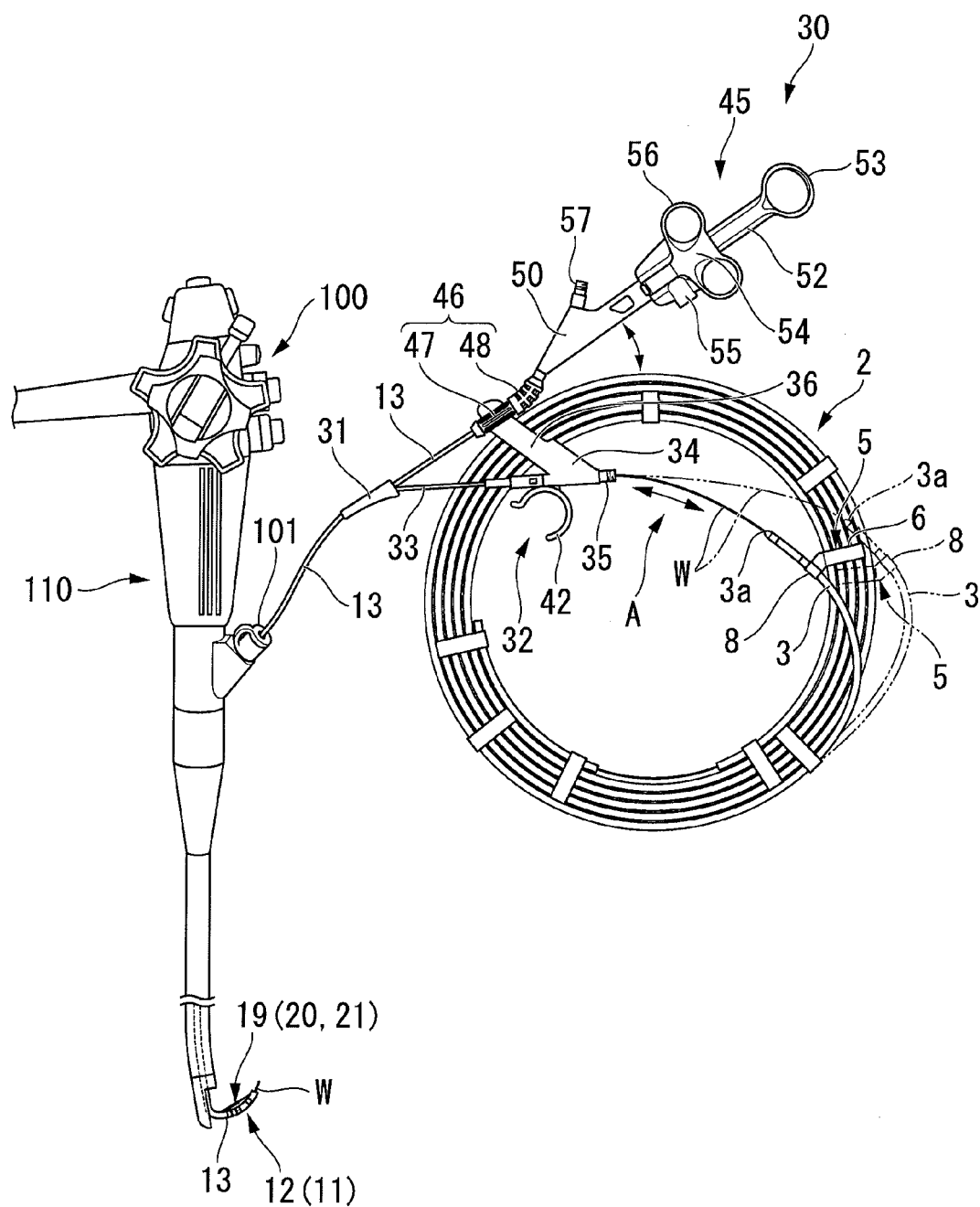
FIG. 14 is an explanatory view for describing a method using the endoscope treatment system.

Additionally, the second concave portion 8 causes the opening 3a, further toward the outer side than the tube member 3 located on an outermost peripheral side of the tube members 3 that are circumferentially (spirally in the present embodiment) wound, to locate as a second attachment aspect in the present embodiment (refer to FIG. 14).

By changing the attachment orientation of the first concave portion 6 with respect to the tube member 3 to attach the holding fixture 5 to the tube member 3, it is possible to switch between the above-described first attachment aspect and second attachment aspect.

Figure 5:
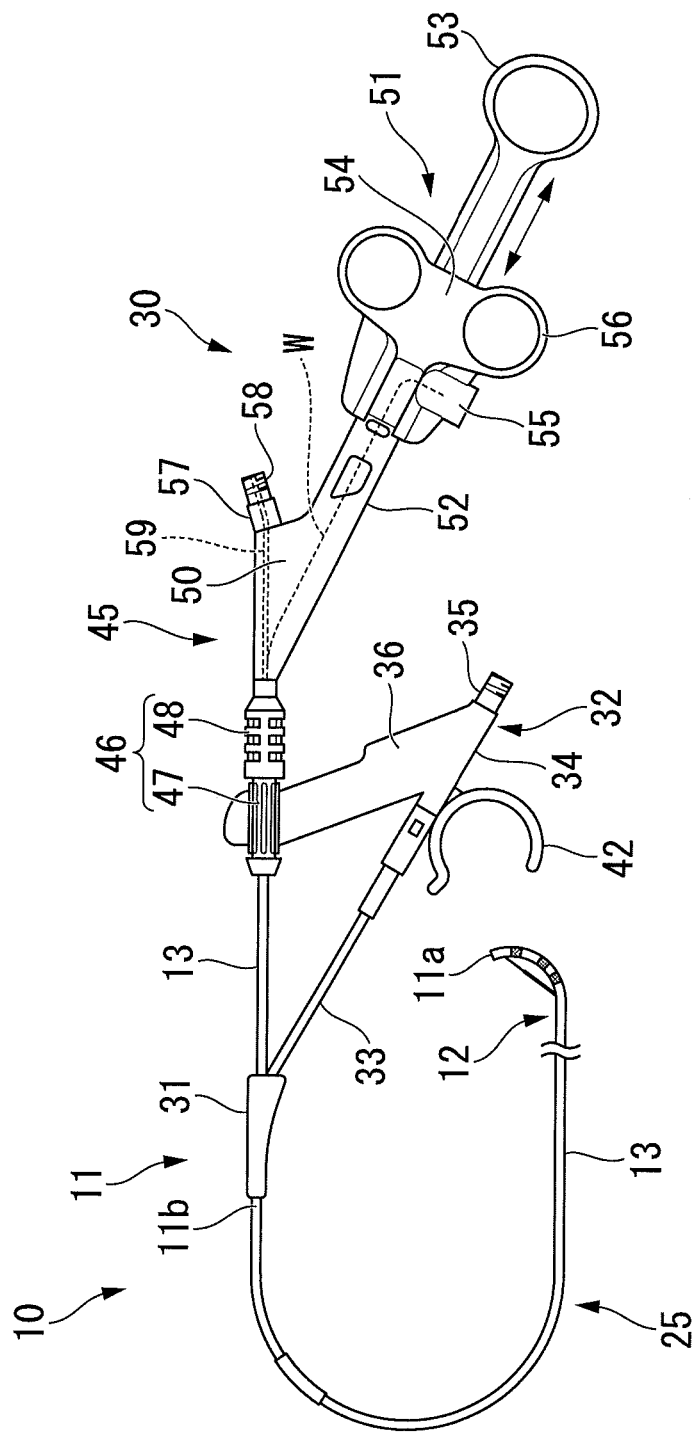
FIG. 5 is a side view of a high-frequency incision tool in the endoscope treatment system.
Figure 6:
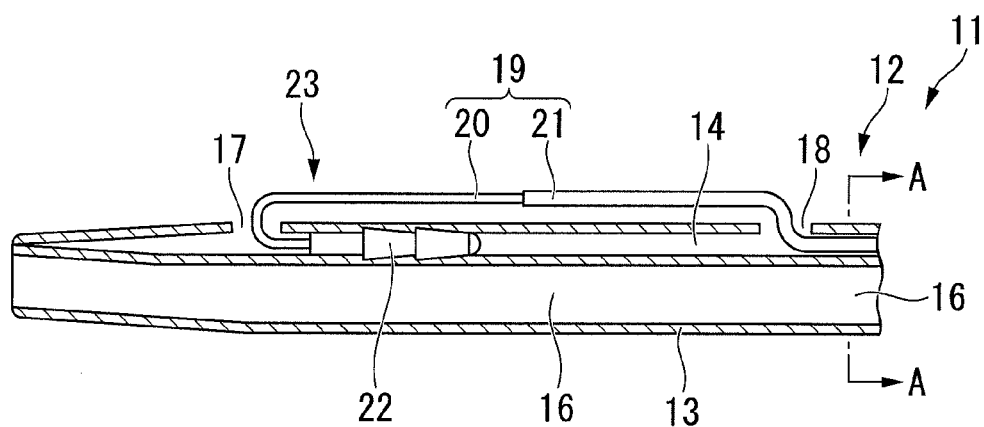
FIG. 6 is a cross-sectional view showing an incision portion in the endoscope treatment system.
Figure 7:
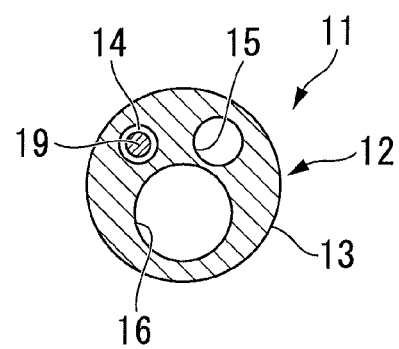
FIG. 7 is a cross-sectional view of a multi-lumen tube in the endoscope treatment system.

Next, the configuration of the high-frequency incision tool 10 will be described. FIG. 5 is a side view of the high-frequency incision tool in the endoscope treatment system. FIG. 6 is a cross-sectional view showing an incision portion in the endoscope treatment system. FIG. 7 is a cross-sectional view of a multi-lumen tube in the endoscope treatment system.

As shown in FIG. 5, the high-frequency incision tool 10 has an insertion section 11 and an operating section 30.

The insertion section 11 is a flexible elongated member having a distal end 11a and a proximal end 11b, and has an incision portion 12 for incising living body tissue, and a sheath portion (sheath) 25 for guiding the incision portion 12 to a region to be incised.

As shown in FIGS. 6 and 7, the incision portion 12 is formed by a multi-lumen tube 13 that has three lumens within one tube. Here, three lumens within the multi-lumen tube 13 are formed with sizes having internal diameters that are different from each other. In the present embodiment, a conductive knife wire 19 for incising living body tissue is inserted through a lumen with the smallest internal diameter (first lumen 14). Additionally, a lumen (second lumen 15) with an internal diameter that is second smallest among the three lumens is used as a conduit line for supplying a fluid, such as a contrast medium. Additionally, a lumen (a third lumen 16) with the greatest internal diameter among the three lumens is used as a conduit line through which the guide wire W is inserted.

Two slits 17 and 18 that communicate with the inside of the first lumen 14 are formed in the lateral wall of the multi-lumen tube 13 on the distal end side. The two slits 17 and 18 are arranged apart from each other in the direction of a longitudinal axis of the multi-lumen tube 13. The knife wire 19 is inserted through the respective slits 17 and 18. That is, a portion of the knife wire 19 on the distal end side is disposed outside the multi-lumen tube 13 through the slits 17 and 18 formed in the lateral wall of the multi-lumen tube 13.

The knife wire 19 has an element wire 20 that has conductivity, and an insulating coating 21 that coats a portion of the element wire 20. A knife tip 22 for fixing the knife wire 19 to a distal end of the first lumen 14 is connected to a distal end of the knife wire 19. The knife tip 22 is press-fitted into the slit 17 located on the distal end side of the two slits 17 and 18 formed in the multi-lumen tube 13, and is fixed within the first lumen 14.

In the knife wire 19, a portion of the knife tip 22 on the proximal end side is an exposed portion 23 that does not have the insulating coating 21. The exposed portion 23 is set to the range of the knife wire 19 that is located outside the multi-lumen tube 13 out of the total length of the knife wire.

The insulating coating 21 is provided further toward the proximal end side than the exposed portion 23 in the knife wire 19. The insulating coating 21 is formed on an outer peripheral surface of the element wire 20 of the knife wire 19 by coating for the purpose of insulation.

The portion of the knife wire 19 closer to the proximal end side than the exposed portion 23 extends toward the proximal end side of the insertion section 11. A proximal end of the knife wire 19 is connected to the operating section 30 (refer to FIG. 5).

As shown in FIG. 5, the sheath portion 25 is provided on the proximal end side of the incision portion 12. Additionally, the sheath portion 25 is a portion that is formed while the multi-lumen tube 13 constituting the incision portion 12 extends to the proximal end side. In the present embodiment, the incision portion 12 and the sheath portion 25 have the multi-lumen tube 13. Accordingly, the sheath portion 25, similar to the incision portion 12, is formed with the first lumen 14, the second lumen 15, and the third lumen 16.

As shown in FIG. 5, the operating section 30 branches to a first operating portion 32 and a second operating portion 45 by the first branching portion 31 connected to the multi-lumen tube 13 that constitutes the sheath portion 25. The first operating portion 32 is pulled out from the first branching portion 31, and has a guide wire tube 33 having flexibility, and a guide wire insertion portion 34 for inserting the guide wire W. In the present embodiment, in the operating section 30, the side that is connected to the sheath portion 25 is a distal end side of the operating section 30.

A distal end side of the guide wire tube 33 communicates with the third lumen 16 (refer to FIG. 7) within the first branching portion 31 and a proximal end side thereof is fixed to the guide wire insertion portion 34.

Figure 8:
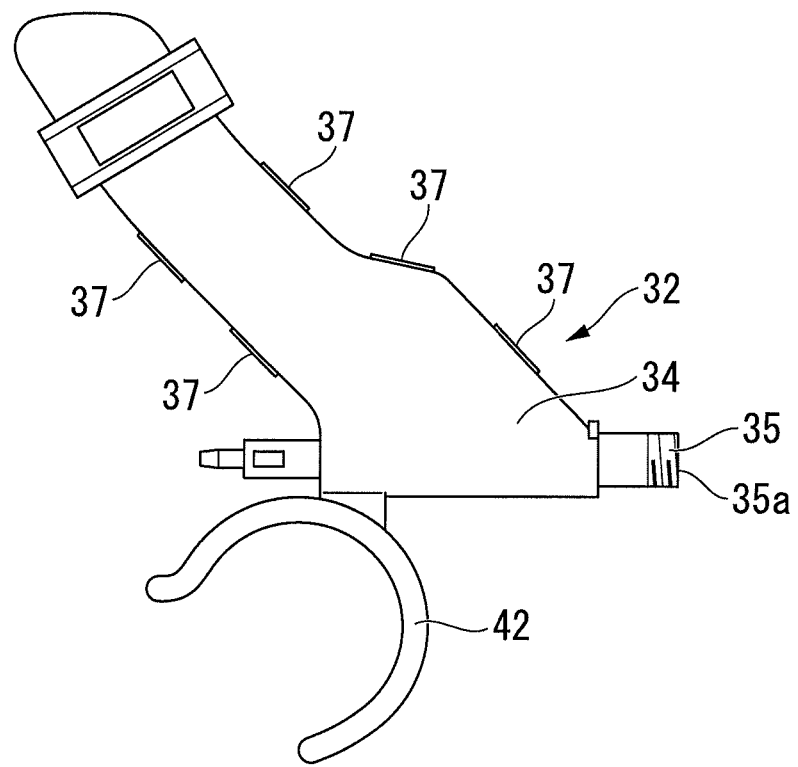
FIG. 8 is a side view showing the configuration of a portion of a guide wire insertion portion in the endoscope treatment system.
Figure 9:
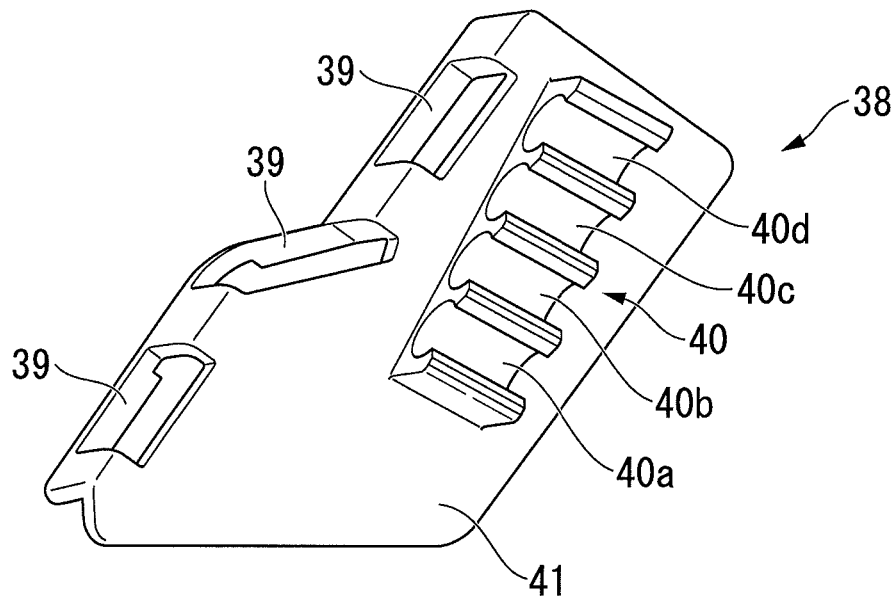
FIG. 9 is a perspective view showing a fixing member attached to the guide wire insertion portion.
Figure 10:
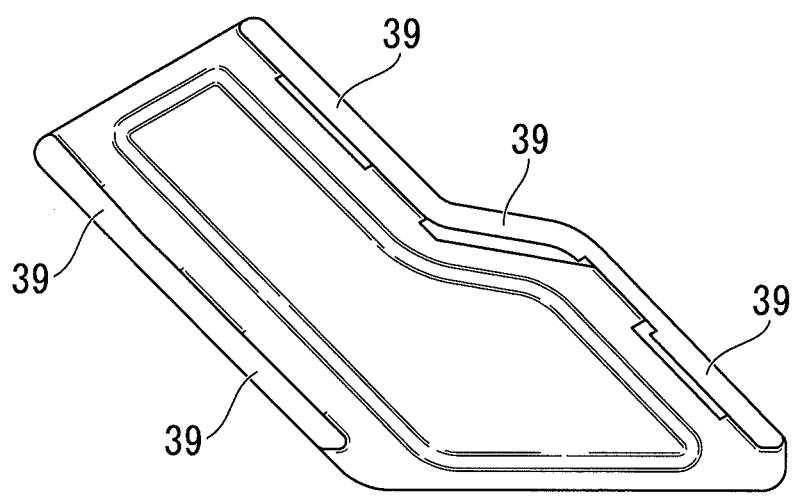
FIG. 10 is a back view of the fixing member.

FIG. 8 is a side view showing the configuration of a portion of the guide wire insertion portion 34 in the endoscope treatment system 1. FIG. 9 is a perspective view showing a fixing member 38 attached to the guide wire insertion portion 34. FIG. 10 is a back view of the fixing member 38.

As shown in FIG. 8, the guide wire insertion portion 34 has the tubular wire insertion port 35 that communicates with the guide wire tube 33, a connecting portion 36 for connecting the guide wire insertion portion 34 to the second operating portion 45, and a second connecting portion 42 for connecting the guide wire insertion portion 34 to an endoscopic apparatus 100.

The connecting portion 36 is formed to protrude in a radial direction of the wire insertion port 35 from an external surface of the wire insertion port 35. The connecting portion 36 has a fixing member 38 (refer to FIG. 9) for fixing the guide wire holder 2 to the operating section 30. As shown in FIG. 8, the connecting portion 36 has projection portions 37 for attaching the fixing member 38.

As shown in FIGS. 9 and 10, the fixing member 38 has locking portions 39 that are lockable to the projection portions 37 formed on the connecting portion 36, and a concave portion 40 that engages the external surface of the tube member 3 that constitutes the guide wire holder 2.

The fixing member 38 couples the operating section 30 to the guide wire holder 2 so that a distal end 30a and a proximal end 30b of the operating section 30 are located outside the circumference of the guide wire holder 2. Additionally, the concave portion 40 provided in the fixing member 38 is engaged with portions, which are adjacent to each other in the tube member 3 that is circumferentially wound, by friction. Additionally, the concave portion 40 has a circular-arc recessed shape that covers more than a semicircle of the external surface of the tube member 3, in the radial cross-section of the tube member 3. The concave portion 40 may be engageable with at least one place of the tube member 3 that is circumferentially wound. That is, the fixing member 38 may have at least one the concave portion 40. If there are two or more concave portions 40, the tube member 3 can be more firmly held. In the present embodiment, the concave portion 40 has four concave portions 40a to 40d that are adjacent to each other.

Additionally, the fixing member 38 may couple the operating section 30 to the guide wire holder 2 so that an opening 35a formed in the wire insertion port 35 and having the guide wire W inserted thereinto is located inside the circumference of the guide wire holder 2.

Additionally, as shown in FIG. 9, the circumference of the portion of the fixing member 38 where the concave portion 40 is formed is a flat planar portion 41. The planar portion 41 supports the tube member 3 so that the planar portion comes into contact with the external surface of the tube member 3 (refer to FIG. 1) and the guide wire holder 2 does not easily oscillate when the endoscope treatment system 1 is used.

As shown in FIG. 8, the second connecting portion 42 is formed in a C-shape that has a circular-arc shape in the same plane that passes through the axis of the guide wire insertion portion 34. The second connecting portion 42 has elasticity and engages an operating section 110 (refer to FIG. 14) of the endoscopic apparatus 100.

As shown in FIG. 5, the second operating portion 45 is connected to a proximal end of the multi-lumen tube 13, which is pulled out through the first branching portion 31, via a connector 46. The connector 46 has a tubular shape that is coaxial with the multi-lumen tube 13. The connector 46 is formed with a connected portion 47 to which the connecting portion 36 formed at the guide wire insertion portion 34 is connected. The connected portion 47 has irregularities to which the connecting portion 36 fits.

Moreover, the connector 46 is provided with a deformable portion 48 that is freely deformed in the direction of an axis thereof. The deformable portion 48 is provided with a second branching portion 50.

The second branching portion 50 is provided in order to branch the first lumen 14 and the second lumen 15 that are provided at the multi-lumen tube 13. The second branching portion 50 is provided with a sliding portion 51 that communicates with the first lumen 14 and a liquid delivery portion 57 that communicates with the second lumen 15.

The sliding portion 51 extends in a direction that inclines with respect to the axis of the connector 46. The sliding portion 51 has a substantially rod-shaped main body 52, and a slider 54 that is slidable in the direction of a lolngitudinal axis of the main body 52. Moreover, the main body 52 is provided with graduations used as indexes that enable the traveling distance of the slider 54 to be confirmed, and a finger-hooking ring 53.

The proximal end of the knife wire 19 is fixed to the slider 54. Additionally, the slider 54 is provided with a plug 55 for applying a high-frequency current to the knife wire 19. The plug 55 is electrically connected to the knife wire 19 inside the slider 54.

Additionally, the slider 54 is provided with the finger-hooking rings 56. An operator of the high-frequency incision tool 10 puts his/her fingers into the ring 53 provided at the main body 52, and into the rings 56 provided at the slider 54 to operate the sliding portion 51. That is, the knife wire 19 can be moved in the direction of the longitudinal axis of the main body 52 by advancing and retracting the slider 54 with respect to the main body 52. For example, if the slider 54 is moved toward a proximal end side of the main body 52, in the incision portion 12 disposed at the distal end of the insertion section 11, the distal end of the multi-lumen tube 13 is pulled to the proximal end side by the knife wire 19 and the distal end of the multi-lumen tube 13 is bent.

The liquid delivery portion 57 has a liquid delivery mouthpiece 58 that is connectable with a syringe, and a conduit line 59 that communicates with the liquid delivery mouthpiece 58 and the second lumen 15 and through which a liquid flows. The liquid delivery mouthpiece 58, for example, may be formed with a projection that adapts to a lock type syringe and may be formed with a surface that can frictionally engage a slip tip type syringe.

Figure 11:
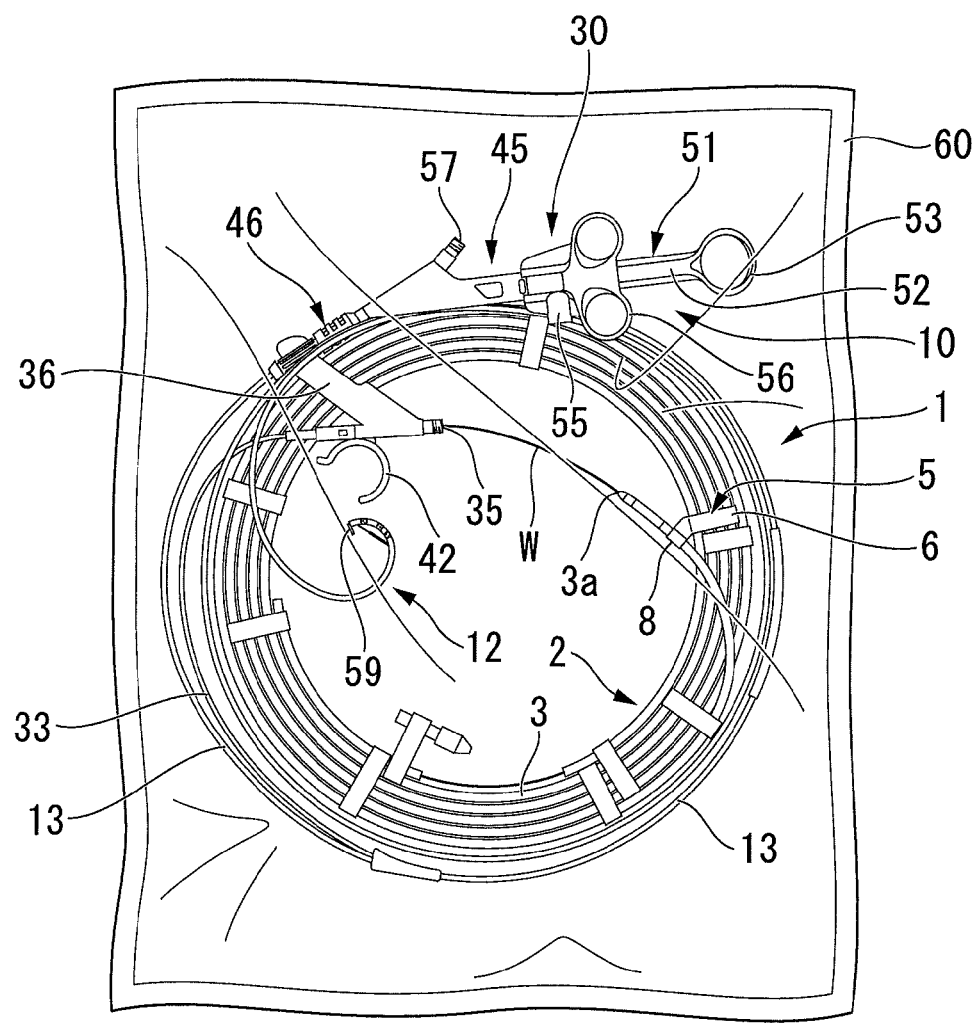
FIG. 11 is a side view showing a state where the endoscope treatment system is stored within a sterilizing pack.
Figure 12:
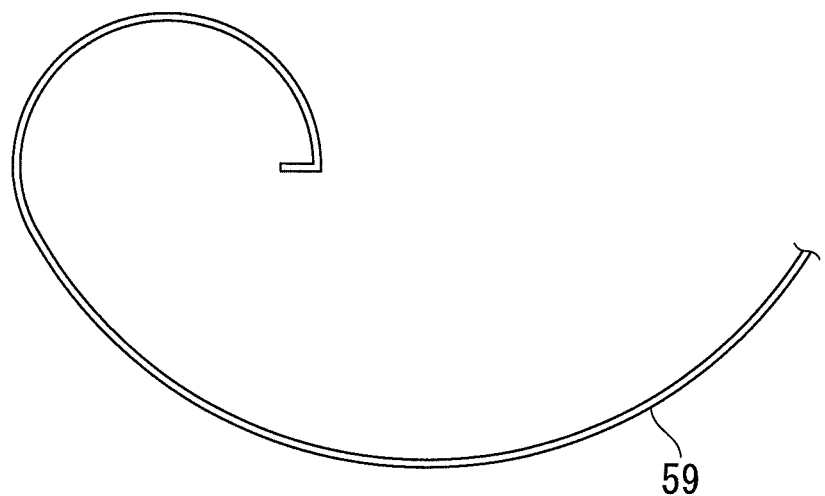
FIG. 12 is a side view showing a pre-curved stylet used when the endoscope treatment system is stored.
Figure 13:
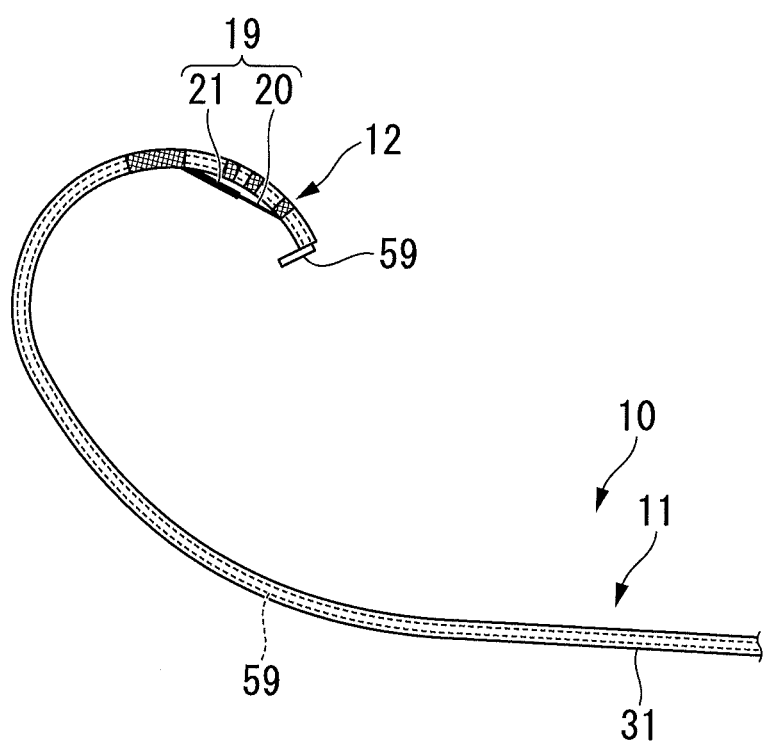
FIG. 13 is a side view showing a state where the pre-curved stylet is attached to the insertion section of the high-frequency incision tool.
Figure 15:
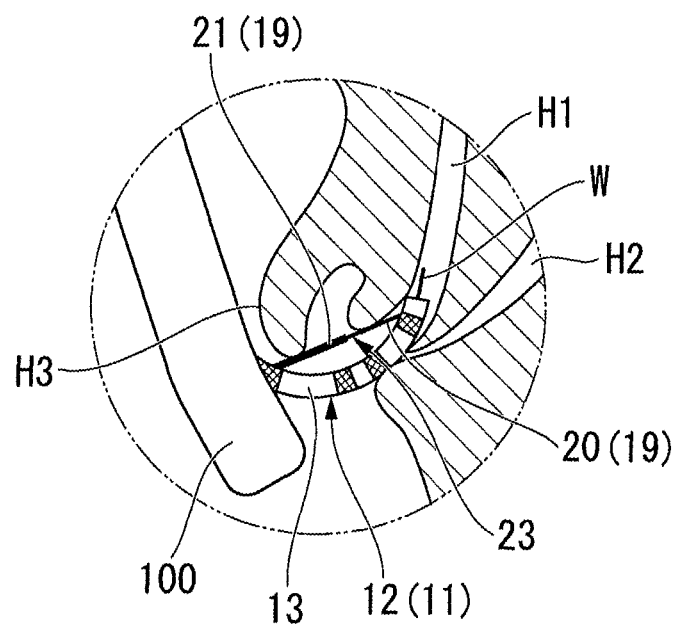
FIG. 15 is a schematic view showing a process of a procedure using the endoscope treatment system.

Next, the use method and operation of the endoscope treatment system 1 of the present embodiment will be described. In the present embodiment, description will be made taking, as an example, a procedure (duodenal papilla sphincter muscle resection (EST)) for incising duodenal papilla in order to discharge into the duodenum a gallstone formed within the bile duct. FIG. 11 is a side view showing a state where the endoscope treatment system 1 is stored within a sterilizing pack 60. FIG. 12 is a side view showing a pre-curved stylet (conduit line) 59 used when the endoscope treatment system 1 is stored. FIG. 13 is a side view showing a state where the pre-curved stylet 59 is attached to the insertion section 11 of the high-frequency incision tool 10. FIG. 14 is an explanatory view for describing a use method of the endoscope treatment system 1. FIG. 15 is a schematic view showing a process of a procedure using the endoscope treatment system 1.

The endoscope treatment system 1, as shown in FIG. 1, is accommodated in the sterilizing pack 60 in a state where the guide wire W is inserted in advance through the third lumen 16 in the multi-lumen tube 13 that constitutes the insertion section 11, and the guide wire holder 2 is fixed to the high-frequency incision tool 10 by the fixing member 38 (refer to FIG. 11). Moreover, when the endoscope treatment system 1 is accommodated within the sterilizing pack 60, the pre-curved stylet 59 for holding the distal end shape of the insertion section 11 in a predetermined bent shape is inserted into the third lumen 16 in the distal end of the insertion section 11.

As shown in FIGS. 12 and 13, the pre-curved stylet 59 is formed from a wire rod harder than the multi-lumen tube 13. The shape of the pre-curved stylet 59 may be appropriately set corresponding to the intended use of the endoscope treatment system 1.

Additionally, as shown in FIG. 11, in the holding fixture 5, the first concave portion 6 is attached to the tube member 3 so that the second concave portion 8 is located inside the circumference of the tube member 3, in a state where the portion of the opening 3a for delivering the guide wire W from the tube member 3 is fixed to the second concave portion 8.

The endoscope treatment system 1 is kept in a sterile condition within the sterilizing pack 60 in a state where the high-frequency incision tool 10, the guide wire holder 2, and the pre-curved stylet 59 are integrally assembled, until the endoscope treatment tool is used. When the endoscope treatment system 1 is stored within the sterilizing pack 60, the second operating portion 45 of the high-frequency incision tool 10 is adjacent to the guide wire holder 2. More specifically, the longitudinal axis of the main body 52 of the second operating portion 45 is turned to a tangential line of the tube member 3 that is circumferentially wound in the guide wire holder 2. In this way, the endoscope treatment system 1 is compactly wound when being stored into the sterilizing pack 60.

When the endoscope treatment system 1 is used, first, the sterilizing pack 60 is opened, and the endoscope treatment system 1 is taken out from the sterilizing pack 60 while holding the high-frequency incision tool 10 or the guide wire holder 2 (Step S1). Subsequently, the pre-curved stylet 59 is taken out from the distal end of the insertion section 11 (Step S2). Thereafter, the second operating portion 45 is held by passing the fingers through the rings 53 and 56 provided in the second operating portion 45 (Step S3). In Step S3, it is a preferable way of use that the guide wire holder 2 is located below the second operating portion 45. That is, the guide wire holder 2 is attached to the operating section 30 in a state where the guide wire holder hangs down from the operating section 30. In holding in such a way, the deformable portion 48 is bent due to the weight of the guide wire holder 2, and the guide wire holder 2 is spaced apart from the operating section 30 as compared to when the endoscope treatment system 1 is stored (refer to FIGS. 11 and 14). Accordingly, a space around the operating section 30 expands.

A high-frequency power source device (not shown) for supplying a high-frequency current to the knife wire 19 is connected to the plug 55 provided at the operating section 30.

An operator inserts the distal end of the insertion section 11 into a treatment tool channel 101 of the endoscopic apparatus 100, and makes the insertion section 11 protrude from the distal end of the treatment tool channel 101. Then, the guide wire W is pushed out toward the distal end of the insertion section 11. At this time, the operator advances and retracts the guide wire W while holding the portion (a portion shown by symbol A in FIG. 14) of the total length of the guide wire W that is exposed between the wire insertion port 35 provided in the operating section 30 and the opening 3a of the tube member 3 from which the guide wire W is delivered.

If necessary, the position of the opening 3a of the tube member 3 from which the guide wire W is delivered may be outside an outermost periphery of the tube member 3 that is circumferentially wound. The position of the opening 3a can be changed by changing the attachment orientation of the first concave portion 6 with respect to the tube member 3.

As shown in FIG. 14, when the opening 3a is located further toward the inner side than an innermost periphery of the tube member 3 that is circumferentially wound, the opening 3a is located near the wire insertion port 35 located inside the circumference, and the opening 3a is turned to the wire insertion port 35. Accordingly, the distance between the wire insertion port 35 and the opening 3a is short, and the curvature of the guide wire W exposed between the wire insertion port 35 and the opening 3a can be made small. Accordingly, when the guide wire W is moved, the guide wire W is not easily buckled, and the guide wire W can be smoothly moved.

In contrast, when the opening 3a is located further toward the outer side than the outermost periphery of the tube member 3 that is circumferentially wound, the exposure length of the guide wire W becomes longer than that in a case where the opening 3a is located inside the circumference of the tube member. Accordingly, the length by which the guide wire W can be moved in one operation becomes longer than that in a case where the opening 3a is located inside the circumference of the tube member.

As shown in FIG. 15, the operator makes the guide wire W protrude from the distal end of the insertion section 11 and inserts the guide wire into the duodenal papilla. The operator pushes the guide wire W while adjusting the position of the guide wire W so that the distal end of the guide wire W enters into the bile duct. Moreover, the distal end of the insertion section 11 is inserted into the duodenal papilla following the guide wire W inserted into the duodenal papilla. Then, the exposed portion 23 of the knife wire 19 is arranged in the vicinity of the papilla sphincter muscle, and a high-frequency current is applied to the knife wire 19. Then, living body tissue that has come into contact with the exposed portion 23 of the knife wire 19 is incised. Further, the operator moves the slider 54 to the proximal end side of the main body 52 and bends the region of the multi-lumen tube 13 on the distal end side. Accordingly, the papilla sphincter muscle is incised in a duodenal papilla H3 by the exposed portion 23 of the knife wire 19, and an opening required in order to take out a gallstone from the inside of a bile duct H 1 is formed in the duodenal papilla H3.

When a pancreatic duct H2 is a treatment target, the guide wire W is inserted into the pancreatic duct H2.

From the above, in the endoscope treatment system 1 of the present embodiment, the main body 52 and the slider 54 of the second operating portion 45 in the operating section 30 are located outside the outermost periphery of the tube member 3 that is circumferentially wound. Thus, when the endoscope treatment system 1 is used, the tube member 3 is not easily touched by an operator's hand, and the tube member 3 does not easily become obstructive.

Moreover, in the present embodiment, when the second operating portion 45 is held by a suitable way to hold the second operating portion 45 in the endoscope treatment system 1, the guide wire holder 2 is brought into the state of hanging down from the operating section 30, and the guide wire holder 2 is spaced apart from the operating section 30 due to the weight of the guide wire holder 2. Also at this point, when the endoscope treatment system 1 is used, the tube member 3 is not easily touched by the operator's hand and the tube member 3 does not easily become obstructive.

Particularly in the present embodiment, as the deformable portion 48 provided at the connector 46 is bent, the distance between the guide wire holder 2 and the operating section 30 is increased. By coupling the second operating portion 45 and the fixing member 38 together via the deformable deformable portion 48 in this way, a compact state where the second operating portion 45 is located near the guide wire holder 2 when the endoscope treatment system 1 is stored occurs, and a state where the guide wire holder 2 is spaced apart from the second operating portion 45 so as not to become obstructive when the endoscope treatment system 1 is used is brought about. That is, the endoscope treatment system 1 of the present embodiment can be compactly stored, and its operativity when being used is excellent.

Additionally, a positional relationship in which the guide wire W is not easily buckled, and a positional relationship in which the traveling distance of the guide wire W that can be moved in one operation can be increased can be appropriately switched according to an operator's request by the holding fixture 5 attached to the guide wire holder 2.

Additionally, since the wire insertion port 35 is located further toward the inner side than the innermost periphery in the tube member 3 that is circumferentially wound, as compared to in a case where the wire insertion port 35 is located further toward the outer side than the outer periphery of the tube member 3 that is circumferentially wound, the endoscope treatment system 1 can be compactly stored in the sterilizing pack 60.

Additionally, since the operating section 30 and the guide wire holder 2 is attachable and detachable by the engagement between the concave portion 40 provided in the fixing member 38 and the tube member 3, when different operators want to hold and use the operating section 30 and the guide wire holder 2, respectively, the operating section 30 and the guide wire holder 2 can be used without being fixed by releasing the engagement state between the concave portion 40 and the tube member 3.

Additionally, since the position of the opening 3a from which the guide wire W is delivered can be switched to the inner side or outer side of the tube member 3 by the second concave portion 8, when the operating section 30 and the guide wire holder 2 are used without being fixed, the operating section and the guide wire holder can be used with the opening 3a being located at a position where operation is easy.

While preferred embodiments of the present invention have been described and illustrated above, it should be understood that these are exemplary of the present invention and are not to be considered as limiting. All the constituent elements described in the above respective embodiments and modification examples can be carried out by appropriate combinations or omissions in the scope of the technical idea of the present invention.

Moreover, although the preferred examples of the present invention have been described above, the present invention is not limited to these examples. Additions, omissions, substitutions, and other modifications can be made without departing from the concept of the present invention. The present invention is not to be considered as being limited by the foregoing description, and is limited only by the scope of the appended claims.

For example, the planar portion formed at the fixing member may be provided so as to be flush with the bottom of the concave portion formed in the fixing member. In this case, the tube member is more stably held by the planar portion to be flush with the bottom of the concave portion, and the guide wire holder does not easily oscillate.

Additionally, in the above-described embodiment, the tube member of the guide wire holder is adapted to elastically deform the tube member, which is more flexible than the fixing member and the holding fixture, so as to be attached to the fixing member or the holding fixture. In addition to such a configuration, the tube member of the guide wire holder may be harder than the fixing member and the holding fixture. In this case, the tube member may be provided with a joint, which bends the tube member in order to change the orientation of the opening from which the guide wire is delivered.

Additionally, the tube member of the guide wire holder may have a portion that is more flexible than the fixing member and the holding fixture and a portion that is harder than the fixing member and the holding fixture.

The invention claimed is:

1. An endoscope treatment system comprising:
an endoscope treatment tool that has (i) an operating section including a distal end and a proximal end, (ii) a sheath that is connected to the distal end of the operating section and is formed with a lumen into which a guide wire is capable of being inserted, and (iii) a first opening that is provided at the operating section so as to communicate with the lumen;
a guide wire holder that (i) has a tube member in which the guide wire is accommodated, (ii) includes a radially inner portion that is wound circumferentially and a radially outermost portion that is wound around the inner portion, the inner portion and the outermost portion being concentrically wound in a circular shape, and (iii) has an end portion with a second opening from which the guide wire is capable of protruding from the tube member;
a fixing member that couples the operating section to the guide wire holder so that the distal end and the proximal end of the operating section are located outside of the outermost portion; and
a holding fixture that holds the end portion of the guide wire holder so that the end portion is biased from the outermost portion toward the inner portion so as to overlap the inner portion and so that the second opening faces the first opening,
wherein the guide wire is exposed between the first opening and the second opening so as to be capable of being operated at a space further radially inward than the inner portion of the guide wire holder.

2. The endoscope treatment system according to claim 1, wherein the fixing member detachably couples the operating section to the guide wire holder.

3. The endoscope treatment system described in claim 2, wherein the fixing member couples the operating section to the guide wire holder so that the first opening is located inside the circumference of the guide wire holder.

4. The endoscope treatment system according to claim 3, wherein the operating section has:
a main body that is formed in a rod shape; and
a slider that is attached to the main body and is configured to slide along a longitudinal axis of the main body, and
wherein the fixing member couples the operating section to the guide wire holder so that the operating section is adjacent to the guide wire holder in a state where the longitudinal axis is turned to a tangential direction of the circumference of the guide wire holder.

5. The endoscope treatment system according to claim 4, wherein the holding fixture is attached to the tube member so as to be capable of switching between a state where the second opening of the tube member is located outside the circumference of the guide wire holder and a state where the second opening of the tube member is located inside the circumference of the guide wire holder.

6. The endoscope treatment system according to claim 5, wherein the operating section and the guide wire holder are detachably coupled by an engagement between (i) a concave portion provided in the fixing member and (ii) the tube member.

7. The endoscope treatment system according to claim 6, wherein the endoscope treatment tool and the guide wire holder are stored in a sterilizing pack in a state where the endoscope treatment tool and the guide wire holder are coupled by the fixing member.

8. The endoscope treatment system according to claim 2, wherein the operating section has:
a main body that is formed in a rod shape; and
a slider that is attached to the main body and is configured to slide along a longitudinal axis of the main body, and
wherein the fixing member couples the operating section to the guide wire holder so that the operating section is adjacent to the guide wire holder in a state where the longitudinal axis is turned to a tangential direction of the circumference of the guide wire holder.

9. The endoscope treatment system according to claim 1, wherein the fixing member couples the operating section to the guide wire holder so that the second opening is disposed closer to the inner portion of the guide wire holder than to the outermost portion.

10. The endoscope treatment system according to claim 9, wherein the holding fixture holds the end portion of the guide wire holder so that second opening is disposed within the circumference of the inner portion of the guide wire holder.

11. The endoscope treatment system according to claim 1, wherein the holding fixture comprises (i) a first part configured to hold a portion of the tube member so that the portion extends in a first direction, and (ii) a second part configured to hold another portion of the tube member so that the another portion extends in a second direction different from the first direction.

12. The endoscope treatment system according to claim 11, wherein the first part of the holding fixture comprises a plurality of concave portions, the axes of the concave portions extending in parallel directions, and
wherein the second part of the holding fixture comprises at least one additional concave portion, an axis of which extends in a direction non-parallel to the axes of the plurality of concave portions constituting the first part.

13. The endoscope treatment system according to claim 12, wherein the at least one additional concave portion of the second part holds the end portion of the guide wire holder.

* * * * *